United States Patent
Sweeney

(10) Patent No.: US 10,653,470 B2
(45) Date of Patent: May 19, 2020

(54) COMPRESSIBLE MIXING AND DELIVERY SYSTEM FOR MEDICAL SUBSTANCES

(71) Applicant: Spinal Generations, LLC, Mokena, IL (US)

(72) Inventor: Patrick J. Sweeney, Flossmoor, IL (US)

(73) Assignee: Spinal Generation, LLC, Mokena, IL (US)

(*) Notice: Subject to any disclaimer, the term of this patent is extended or adjusted under 35 U.S.C. 154(b) by 1261 days.

(21) Appl. No.: 14/184,478

(22) Filed: Feb. 19, 2014

(65) Prior Publication Data

US 2015/0230846 A1    Aug. 20, 2015

(51) Int. Cl.
*A61B 17/88* (2006.01)
*A61M 5/32* (2006.01)
(Continued)

(52) U.S. Cl.
CPC ...... *A61B 17/8816* (2013.01); *A61B 17/3472* (2013.01); *A61B 17/8822* (2013.01);
(Continued)

(58) Field of Classification Search
CPC .. A61M 5/3294; A61M 2210/02; A61M 5/48; A61M 2202/07; A61B 17/8816;
(Continued)

(56) References Cited

U.S. PATENT DOCUMENTS

| | | | |
|---|---|---|---|
| 3,310,051 A | | 3/1967 | Schulte |
| 3,870,198 A | * | 3/1975 | Cohen ............... B65D 83/0066 222/104 |

(Continued)

FOREIGN PATENT DOCUMENTS

| | | |
|---|---|---|
| EP | 0 858 775 | 8/1998 |
| EP | 1 653 869 A1 | 6/2011 |

(Continued)

OTHER PUBLICATIONS

European Office Action for Application No. 04757057.7, dated Jan. 26, 2010, 5 pages.

(Continued)

*Primary Examiner* — Paul B Prebilic
(74) *Attorney, Agent, or Firm* — Foley & Lardner LLP

(57) ABSTRACT

A method of mixing and delivering a substance to a bone includes providing a compressible tube having a reservoir and using a mixing apparatus to mix a particulate solid and a mixing liquid to form the substance within the reservoir of the compressible tube. The method further includes using a compressing device to move the substance through an exit port in the compressible tube for delivery to the bone. The compressing device may be positioned on the compressible tube and the method may further include moving the compressing device along the compressible tube to empty the substance from the compressible tube. The substance may be a bone void filler, and the substance may be delivered from the exit port in the tube through a delivery apparatus, such as a cannula, to a target portion of the anatomy.

12 Claims, 7 Drawing Sheets

(51) Int. Cl.
*B01F 13/00* (2006.01)
*B01F 15/00* (2006.01)
*B01F 15/02* (2006.01)
*A61B 17/34* (2006.01)
*A61B 17/00* (2006.01)

(52) U.S. Cl.
CPC ....... *A61B 17/8833* (2013.01); *A61M 5/3294* (2013.01); *B01F 13/002* (2013.01); *B01F 15/00006* (2013.01); *B01F 15/0085* (2013.01); *B01F 15/029* (2013.01); *A61B 2017/00495* (2013.01); *A61B 2017/8838* (2013.01); *A61M 2210/02* (2013.01)

(58) Field of Classification Search
CPC ........ A61B 17/8822; A61B 2017/8838; A61B 2560/04; A61B 2560/06; A61B 17/8833; A61B 17/3431
See application file for complete search history.

(56) References Cited

U.S. PATENT DOCUMENTS

| | | | |
|---|---|---|---|
| 4,399,814 A | 8/1983 | Pratt et al. | |
| 4,464,178 A | 8/1984 | Dalton | |
| 4,653,487 A | 3/1987 | Maale | |
| 4,653,489 A | 3/1987 | Tronzo | |
| 4,760,844 A | 8/1988 | Kyle | |
| 4,772,261 A | 9/1988 | Von Hoff et al. | |
| 4,976,692 A | 12/1990 | Atad | |
| 5,047,030 A | 9/1991 | Draenert | |
| 5,203,770 A | 4/1993 | Wigness et al. | |
| 5,380,319 A | 1/1995 | Saito et al. | |
| 5,425,723 A | 6/1995 | Wang | |
| 5,586,821 A * | 12/1996 | Bonitati | A61B 17/8825 366/139 |
| 5,618,286 A | 4/1997 | Brinker | |
| 5,681,289 A | 10/1997 | Wilcox et al. | |
| 5,702,372 A | 12/1997 | Nelson | |
| 5,749,883 A | 5/1998 | Halpern | |
| 5,800,407 A | 9/1998 | Eldor | |
| 5,842,785 A * | 12/1998 | Brown | A61B 17/8825 366/139 |
| 5,871,484 A | 2/1999 | Spievack et al. | |
| 5,876,116 A * | 3/1999 | Barker | A61B 17/8825 222/241 |
| 5,951,160 A | 9/1999 | Ronk | |
| 6,019,761 A | 2/2000 | Gustilo | |
| 6,048,343 A | 4/2000 | Mathis et al. | |
| 6,077,265 A | 6/2000 | Werding et al. | |
| 6,210,376 B1 | 4/2001 | Grayson | |
| 6,214,012 B1 | 4/2001 | Karpman et al. | |
| 6,220,888 B1 | 4/2001 | Correa | |
| 6,228,088 B1 | 5/2001 | Miller et al. | |
| 6,286,670 B1 * | 9/2001 | Smith | A61B 17/8833 206/219 |
| 6,364,856 B1 | 4/2002 | Ding et al. | |
| 6,387,098 B1 | 5/2002 | Cole et al. | |
| 6,461,327 B1 | 10/2002 | Addis et al. | |
| 6,679,890 B2 | 1/2004 | Margulies et al. | |
| 7,018,089 B2 * | 3/2006 | Wenz | A61M 5/31511 206/219 |
| 7,527,611 B2 | 5/2009 | Sweeney | |
| 7,575,572 B2 | 8/2009 | Sweeney | |
| 7,608,062 B2 | 10/2009 | Sweeney | |
| 8,057,090 B1 | 11/2011 | Saha et al. | |
| 8,062,270 B2 | 11/2011 | Sweeney | |
| 8,808,337 B2 | 8/2014 | Sweeney | |
| 2001/0021852 A1 | 9/2001 | Chappius | |
| 2002/0138146 A1 | 9/2002 | Jackson | |
| 2003/0045885 A1 | 3/2003 | Margulies et al. | |
| 2003/0083662 A1 | 5/2003 | Middleton | |
| 2003/0139751 A1 | 7/2003 | Evans et al. | |
| 2003/0212426 A1 | 11/2003 | Olson et al. | |
| 2004/0225292 A1 | 11/2004 | Sasso et al. | |
| 2005/0015059 A1 | 1/2005 | Sweeney | |
| 2005/0015060 A1 | 1/2005 | Sweeney | |
| 2005/0059972 A1 | 3/2005 | Biscup | |
| 2005/0111300 A1 * | 5/2005 | Nies | A61B 17/8822 366/332 |
| 2006/0111767 A1 | 5/2006 | Olson et al. | |
| 2007/0073295 A1 | 3/2007 | Biedermann et al. | |
| 2007/0083265 A1 | 4/2007 | Malone | |
| 2008/0039846 A1 | 2/2008 | Lee et al. | |
| 2008/0039855 A1 | 2/2008 | Lambert | |
| 2008/0086143 A1 | 4/2008 | Seaton et al. | |
| 2009/0164016 A1 | 6/2009 | Georgy et al. | |
| 2009/0204158 A1 | 8/2009 | Sweeney | |
| 2010/0042214 A1 | 2/2010 | Nebosky et al. | |
| 2010/0106199 A1 | 4/2010 | Sawa et al. | |
| 2010/0131014 A1 | 5/2010 | Peyrot et al. | |
| 2010/0262089 A1 | 10/2010 | Sweeney | |
| 2012/0029432 A1 | 2/2012 | Sweeney | |
| 2012/0041395 A1 | 2/2012 | Sweeney | |

FOREIGN PATENT DOCUMENTS

| | | | | |
|---|---|---|---|---|
| WO | WO 90/13264 A | * | 11/1990 | ......... A61B 17/8825 |
| WO | WO-02/098307 A1 | | 12/2002 | |
| WO | WO-2005/009258 A1 | | 2/2005 | |
| WO | WO-2010/019788 | | 2/2010 | |
| WO | WO2013150476 A1 | * | 4/2013 | ......... A61B 17/8822 |

OTHER PUBLICATIONS

European Search Report for European Patent Application No. 04757057.7, dated Nov. 30, 2009, 3 pages.
European Search Report for European Patent Application No. 11250603.5-2310, dated Sep. 29, 2011, 6 pages.
International Search Report and Written Opinion for International Application No. PCT/US2014/035542, dated Sep. 22, 2014, 14 pages.
International Search Report and Written Opinion for PCT Application PCT/US2013/052853, dated Jan. 14, 2014, 15 pages.
Sato, T. et al., "Calcium Phosphate Augmentation of Screw Fixation in Femoral Neck Fracture," 47th Annual Meeting, Orthopaedic Research Society, Feb. 25-28, 2001, San Francisco, CA, 1 page.
Communication received in European Patent Application No. 11250603.5, dated Feb. 20, 2015, 5 pages.
International Search Report and Written Opinion for PCT Application No. PCT/US2015/014216, dated Apr. 22, 2015, 14 pages.

* cited by examiner

COMPRESSIBLE MIXING AND DELIVERY SYSTEM FOR MEDICAL SUBSTANCES

BACKGROUND

The present invention relates generally to the field of devices and methods for delivering substances to bone. More particularly, the present invention concerns devices and methods for mixing and delivering substances to the interior of fractured or otherwise injured bones, especially to the fracture interface.

Present methods of preparing a viscous surgical substance, such as a bone void filler, to be introduced to fractured or injured bones involve cumbersome, multi-step processes. The process to form such a surgical substance requires mixing a bulking agent with a reacting agent to form the substance at the time of use, such as at the time of delivery to the targeted area of the bone. Such methods may require mixing the elements in a separate mixing container and manually transferring the material to a delivery container, such as a syringe. Not only is this method laborious, but can also create a mess at the mixing site. The amount of time used to mix the elements and make this transfer can also add to the increased viscosity of the substance, and make compression of the syringe or delivery device for delivering the substance to a cannula or other delivery apparatus more difficult. Syringes can fail, which may result in waste of the substance therein, or require a further transfer and additional clean-up. Furthermore, the compressive forces necessary to make the transfer from the syringe can be difficult for many users and preparers of the material.

SUMMARY

Various embodiments of the invention described herein allow for mixing and delivery of a substance (e.g., medication or bone void filler) to be delivered to a target area of the body, such as a fracture site after stabilization of the bone.

One embodiment of the invention relates to method of mixing and delivering a substance to a bone including providing a compressible tube having a reservoir and using a mixing apparatus to mix a particulate solid and a mixing liquid to form the substance within the reservoir of the compressible tube. The method further includes using a compressing device to move the substance through an exit port in the compressible tube for delivery to the bone.

The method may also include providing the particulate solid in the reservoir of the compressible tube, or alternatively, introducing the particulate solid into the reservoir of the compressible tube. The method may also include introducing the mixing liquid into the reservoir of the compressible tube. The mixing liquid may be introduced to the reservoir through a sealable inlet portion. The compressible tube may include a portal serving as the inlet portion and the exit port.

The method may also include moving the substance through the exit port and into a delivery apparatus for delivery directly to the bone. The delivery apparatus may be a cannula positioned within the body and having a distal portion position near the target portion of the anatomy.

The substance may be a bone void filler. The compressing device may be positioned on the compressible tube and the method may further include moving the compressing device along the compressible tube to empty the substance from the compressible tube. The compressing device may include a rolling key to roll the compressible tube to empty the substance from the compressible tube.

Another embodiment of the invention relates to a mixing and delivery system including a compressible tube having a reservoir configured for mixing and holding a surgical substance. The compressible tube includes an inlet portion for accommodating the introduction of an element of the surgical substance into the compressible tube. The compressible tube also includes an exit port for enabling the delivery of the surgical substance to a target portion of an anatomy. The system further includes a mixing apparatus configured to be received through the inlet portion of the compressible tube for mixing the elements of the surgical substance to form the surgical substance.

The mixing and delivery system may also include a compressing device configured to move along the compressible tube and force the surgical substance through the exit port. The exit port may be configured to engage with a delivery apparatus which delivers the surgical substance to the anatomy. The delivery apparatus may be a cannula positioned within the body and having a distal portion position near the target portion of the anatomy. The inlet portion may be sealable. The compressible tube may further include a portal serving as the inlet portion and the exit port.

The reservoir of the compressible tube may contain a particulate substance and the fluid introduced through the inlet portion may be a mixing liquid. The surgical substance may be a bone void filler.

Yet another embodiment of the invention relates to a kit for mixing and delivering a surgical substance to an anatomy including a compressible tube having a reservoir configured for mixing and holding the surgical substance, the compressible tube containing a particulate solid. The compressible tube includes a portion capable of being opened to receive a mixing liquid introduced into the reservoir. The compressible tube also includes an exit port for enabling the delivery of the surgical material to a target portion of an anatomy. The kit further includes a mixing apparatus configured to be inserted into the compressible tube for mixing the particulate solid and the mixing liquid. The kit may include a plurality of compressible tubes. The kit may also include at least one compressing device configured to ride along the compressible tube and force the surgical substance through the exit port.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Figure 1:
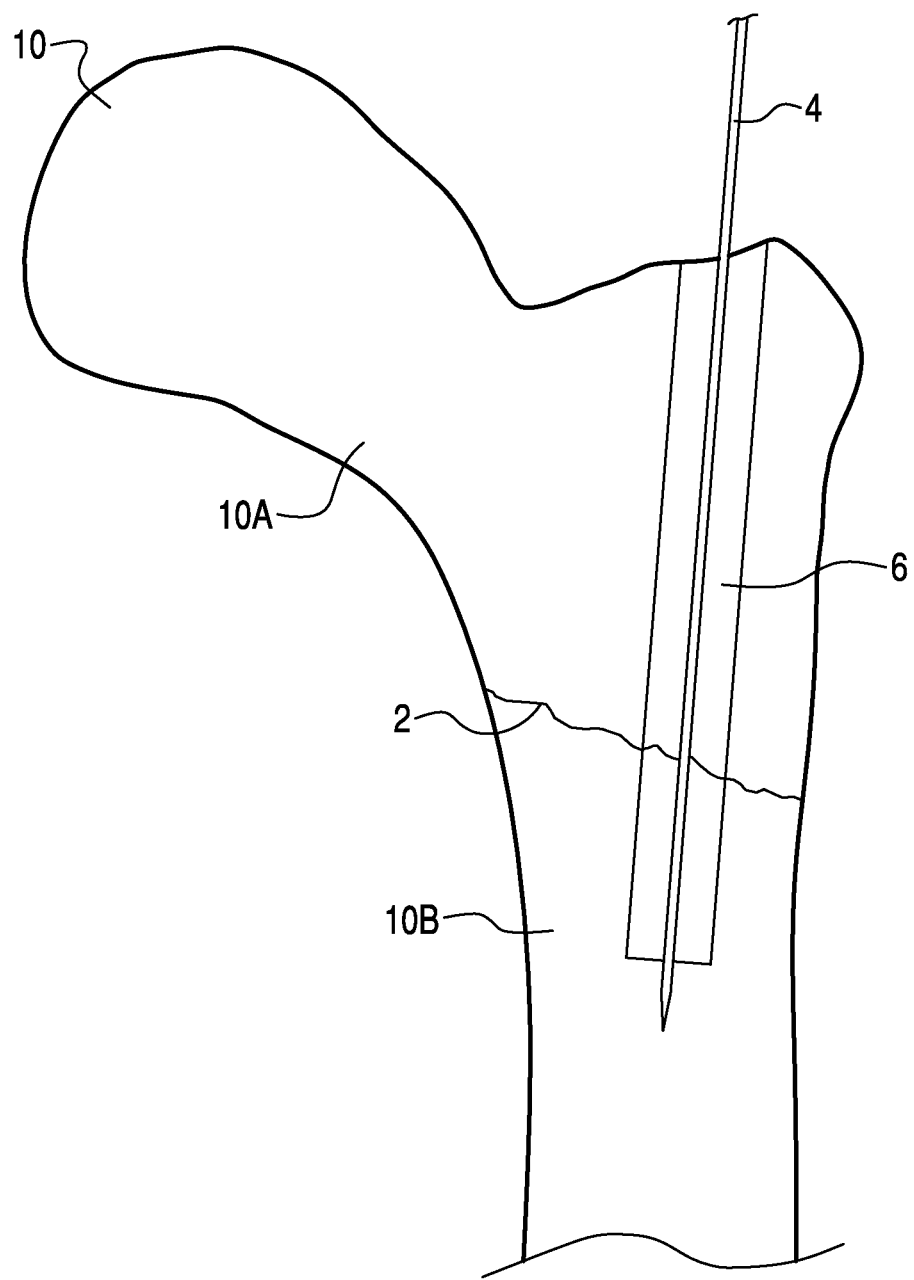
FIG. 1 illustrates a bone with a stabilizing wire and a hole in the bone around the stabilizing wire.

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting. For example, a femur is illustrated in the drawings, but the devices and methods described herein may be used in connection with any bone in the body, including but not limited to bones in the spine, arms, hands, legs, and feet. Furthermore, it should be understood that the exemplary embodiments described herein can also be used for the storage and mixing of other materials and substances. For example, though the description is directed to storing, mixing, and delivery of bone void fillers and similar substances, the delivery system disclosed herein may also be used for the storage of stem cells or bone marrow aspirate, and may accommodate mixing with other substances upon harvesting or at the time of delivery.

Referring to FIG. 1, a bone 10 includes a fracture 2. The fracture 2 separates the bone into portions 10A and 10B. In surgical procedures to repair fractured bones, a stabilizing wire 4 may be used to hold bone portions together. The stabilizing wire 4 may be any type of wire used to temporarily or permanently secure portions of bone together, such as Kirschner wires or Steinmann pins. The stabilizing wire 4 is often placed in a fractured bone 10 prior to insertion of a more permanent bone implant, such as a bone screw, nail, or other fixation structure. In addition to stabilizing the bone portions 10A and 10B, the stabilizing wire 4 may serve as a guide for a cannula, drill or bone implant.

Various delivery apparatuses can be introduced over the stabilizing wire 4 to deliver a surgical substance, such as a bone void filler to the fractured area of the bone, or other target area of the anatomy. Such delivery apparatuses may be elongated cannulas that carry the surgical substance from the fluid/substance source, to the target area of the anatomy, and may be such cannulas as described in U.S. patent application Ser. No. 13/270,072, titled "Method and Device for Delivering Medicine to Bone," filed Oct. 10, 2011, and hereby incorporated by reference herein in its entirety.

Figure 2:
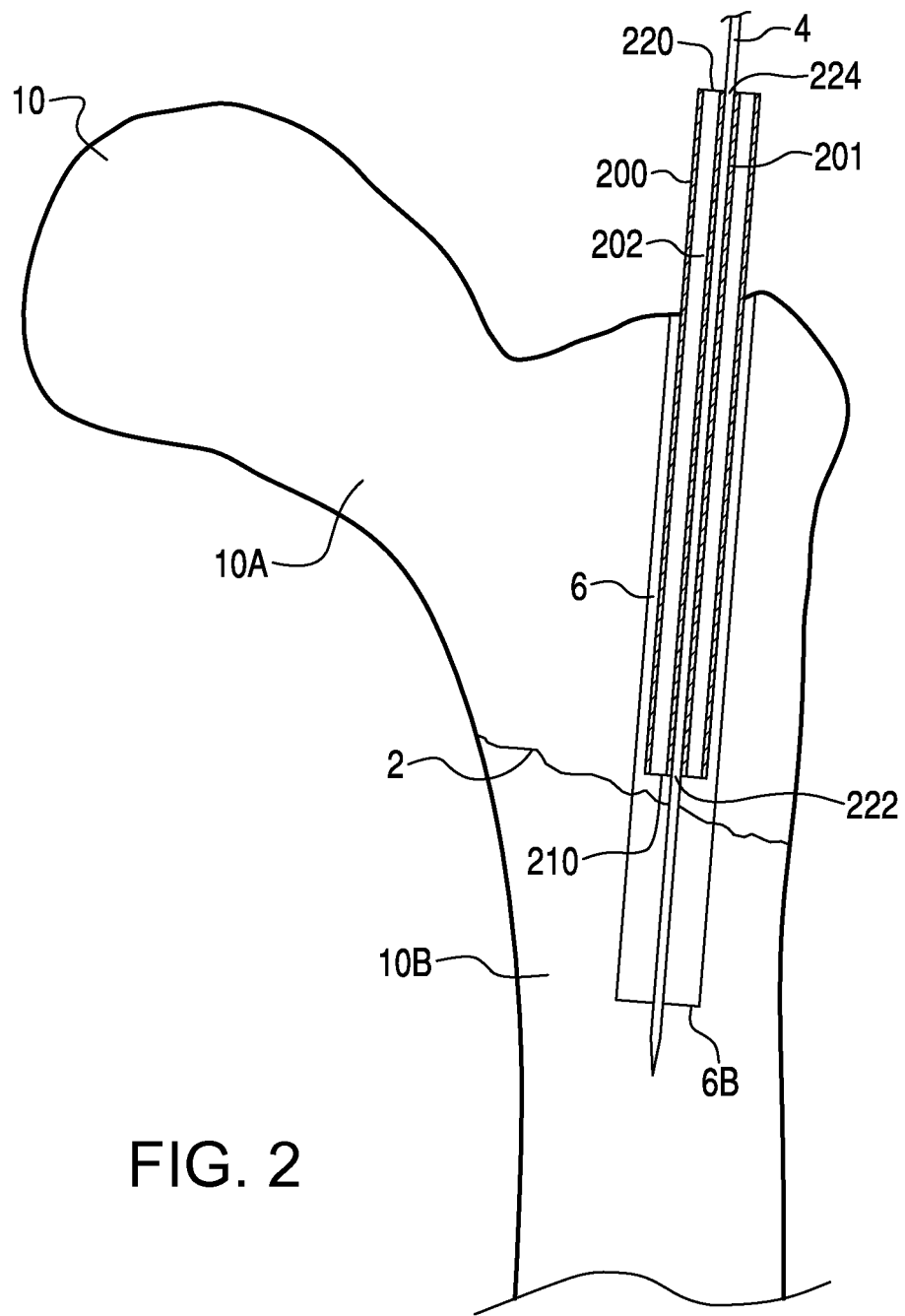
FIG. 2 illustrates the bone and stabilizing wire shown in FIG. 1 with a cannula introduced over the stabilizing wire, for delivery of a surgical substance to a fracture in the bone.

Referring to FIG. 2, according to an exemplary embodiment, a multichannel cannula 200 having, in a preferred embodiment, two or more channels may be introduced over the stabilizing wire 4 to deliver substances to the interior of bone 10. In one embodiment, the multichannel cannula is introduced over the stabilizing wire 4 after creation of hole 6, but prior to placement of a bone implant into the hole 6. A first channel of the multichannel cannula receives the stabilizing wire 4. The other channels of the multichannel cannula may be used for delivering the surgical substance to the interior of bone 10. The substance delivered using the multichannel cannulas described herein may be any type of substance a user desires to deliver to the interior of a bone, including growth factors or medication such as bone void fillers, calcium phosphate paste, an antibiotic, pain medication, or a chemotherapeutic agent.

The cannulas described herein can be made of any material suitable for placement into a bone without harmful effects on the patient. In one embodiment, the cannula is made of stainless steel or other type of metal. In another embodiment, the cannula is made of a rigid plastic, such as polyethylketone, that cannot be easily bent or manipulated into alternative configurations. A rigid cannula may be advantageous to provide stability when introducing the cannula into a hole 6 in a bone 10. Furthermore, a rigid cannula provides stability for various procedures that a more flexible cannula may not provide. For example, if a surgeon desires to use a plunger or other device to push a substance from the cannula and into the bone, a rigid cannula may be more desirable. As another example, a rigid cannula is able to withstand more significant forces than a flexible cannula (e.g., forces applied to the cannula by a delivery device or a suction device, and the forces resulting from movement of substances through the channels and through any open portals in the cannula).

The cannulae that may be used to deliver the substance to the bone are substantially elongated structures with, in preferred embodiments, two or more channels. The multichannel cannula 200 depicted in FIG. 2 and described herein includes a first channel 201 having an open proximal end 224 and an open distal end 222. The open proximal end and open distal end allow the first channel to be threaded over a stabilizing wire 4. Thus, the first channel 201 is configured to receive a stabilizing wire 4. In one embodiment, the first channel 201 is substantially cylindrical and has a diameter slightly larger than the diameter of the stabilizing wire. The side wall of the cylindrical first channel (as distinguished from the open ends of the first channel) may be continuous, meaning there are no open portals or other openings along the side wall of the first channel. In one embodiment, liquid cannot penetrate the side wall of the first channel.

The multichannel cannula shown in FIG. 2 further includes a second channel 202. The second channel 202 includes at least one inlet portal 220 and at least one exit portal (e.g., open distal end 210). In some methods described herein, the inlet portal 220 of the second channel 202 serves as an inlet for the surgical substance to be delivered to the interior of a bone. In these embodiments, the exit portal 210 of the second channel serves as an outlet for the substance. The inlet portal and exit portal of the second channel are thus in fluid communication to allow substances or materials to be delivered to the interior of a bone.

Figure 3:
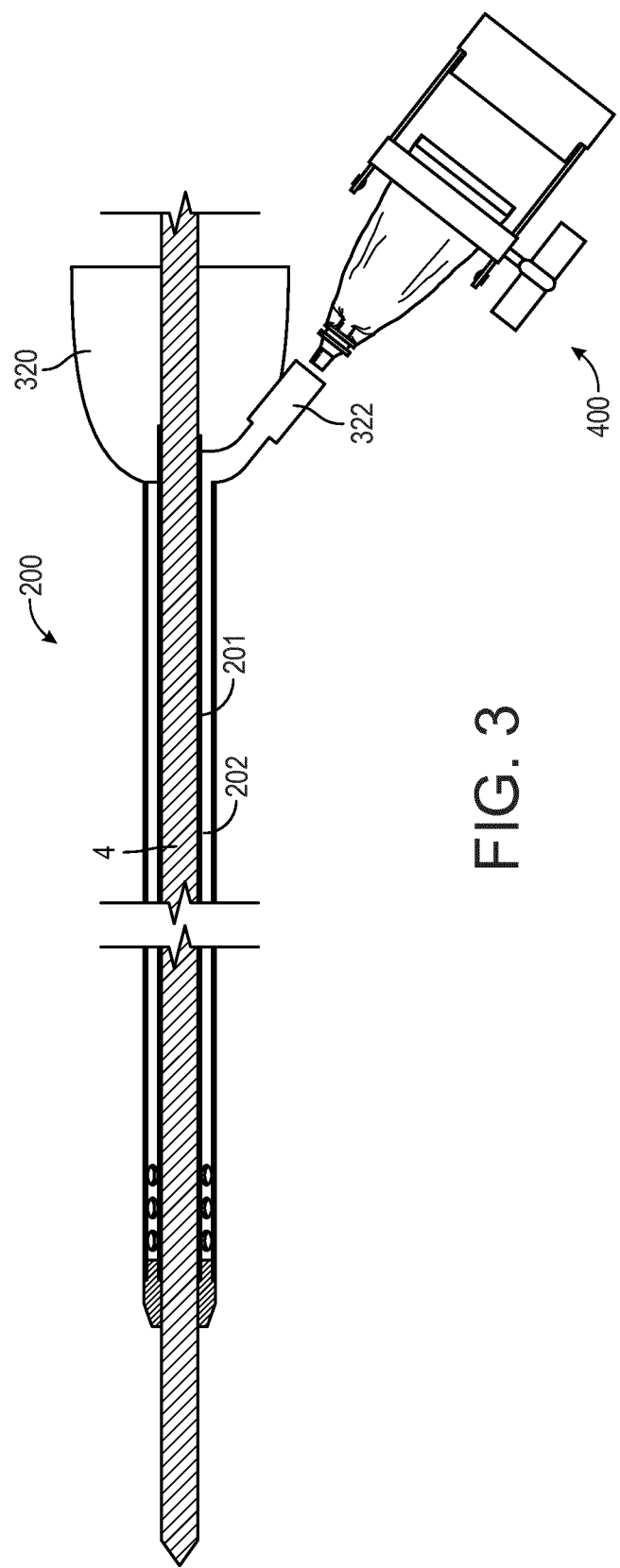
FIG. 3 illustrates a longitudinal section view of a cannula with a cap used in connection with a delivery system according to an exemplary embodiment.

As shown in FIG. 3, multichannel cannula 200 may also include a cap 320. The cap 320 has a housing portion with a channel for coupling to a portion of the proximal end of cannula 200. The channel of the cap 320 may extend from first end through a second end of the housing portion for receiving the stabilizing wire 4 therethrough. In a preferred embodiment, the cap 320 is affixed to the multichannel cannula 200, such as during production of the cannula 200. In an alternative embodiment, the cap 320 may be removable. The cap 320 may be positioned at the site of the hole in the bone, such as hole 6, in order to serve as a plug. In this way, cap 320 can plug the hole 6 and may prevent irrigation or other substance being delivered to the site from coming back up through the hole 6 in the bone. In another embodiment, a separate temporary plug or seal may be added to the cannula to plug the hole 6 in the bone. In the embodiment shown, cap 320 also has a delivery portal 322. The delivery portal 322 is coupled to an inlet portal of the second channel 202 such that a substance can flow from the delivery portal 322, through the inlet portal, and into the second channel 202.

Various delivery systems can be coupled to the delivery portal 322 to assist in delivering substances to the second channel 202 of multichannel cannula 200, and ultimately to the bone. Tubing may be used to connect the delivery system to the delivery portal 322. The type of delivery system selected by a user may depend on the type of substance to be delivered to the bone.

One such delivery system is a mixing and delivery system 400, as depicted in FIGS. 3-7. While shown in use with the cannula 200, the delivery system 400 according to various exemplary embodiments can also be used with other delivery apparatuses, other than the cannulas shown and described above, such as a different cannula, a catheter, or a delivery needle.

Figure 4:
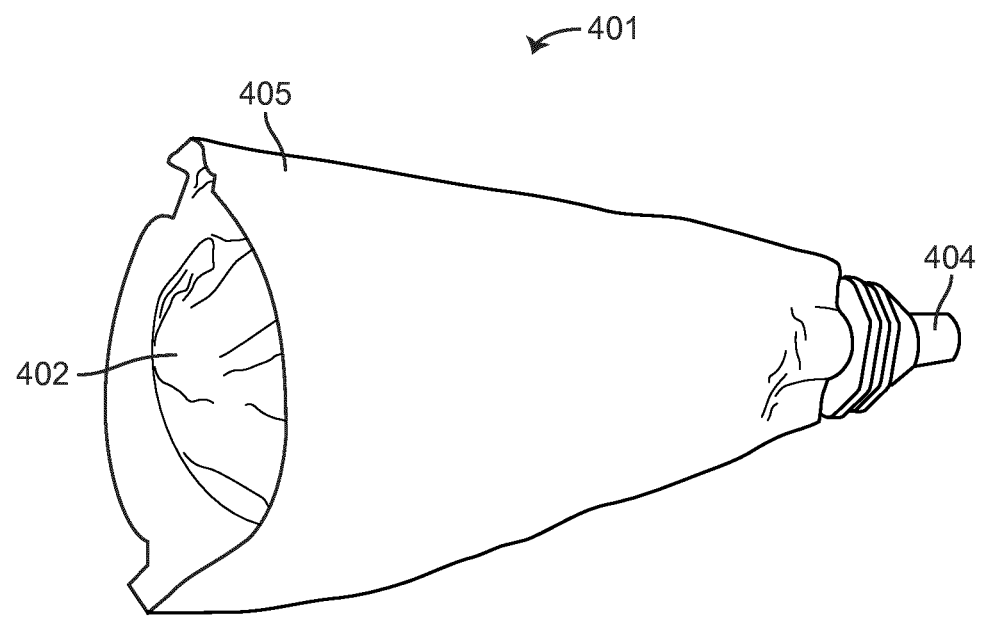
FIG. 4 illustrates a compressible delivery tube according to an exemplary embodiment.

As shown in FIG. 4, the mixing and delivery system 400 includes a flexible, compressible tube 401. The compressible tube 401 includes a reservoir 402 that is configured to hold and/or receive elements to be mixed together for forming a surgical substance. In one embodiment, the elements for forming a bone void filler are a particulate substance and a mixing liquid, such as a bulking agent and a reacting agent. In another embodiment, one of the elements may be a component containing stem cells or bone marrow aspirate that may be mixed with a second element at the time of harvest, or prior to delivery. In yet another embodiment, the first element may be a prepared paste or fluid, to be mixed with a second fluid element. The reservoir 402 is of sufficient size and shape such that the mixing of the elements to form the surgical substance can take place therein. The reservoir 402 is in fluid communication with at least one portal 404 of the compressible tube 401. The portal 404 may serve as both an inlet and an exit portal, or the delivery tube may have more than one portal, one serving as an inlet portion separate from and in addition to an exit portal. The portal 404, or an alternative inlet portion such as a sealable opening, allows for introduction of, for example, the mixing liquid to the particulate solid held in the reservoir 402. The portal 404 is preferably sealable so as to contain the first element, such as a particulate solid, and/or the surgical substance within the reservoir when introduction of the second element, such as the mixing liquid, or delivery of the surgical substance is not taking place. The compressible tube 401 also has an exit portal, which may also be portal 404, through which the mixed and prepared surgical substance is delivered to a delivery apparatus, such as the cannula 200 discussed herein, directly to a target area, or to another device to hold the surgical substance.

In an exemplary embodiment, the portal 404 is both the inlet and the exit portal. In an alternative exemplary embodiment, the portal 404 serves as an exit portal only, and the opposing end 405 is open, or able to be opened and resealed, such that introduction of the mixing liquid and performance of the mixing (described below) can be accomplished through the opposing end 405.

In certain embodiments, the compressible tube 401 has a false bottom, wherein the tube has an internal partition constituting a wall of the reservoir 402 portion of the compressible tube 401. In other embodiments, the reservoir 402 comprises the entirety of the area within the compressible tube 401 structure. The compressible tube 401, in preferred embodiments, is made of a transparent material to enable visualization of the mixing of the surgical substance. In this way, a practitioner is able to witness and guide the progress of the mixing and determine when the surgical substance is appropriately formed.

Figure 5:
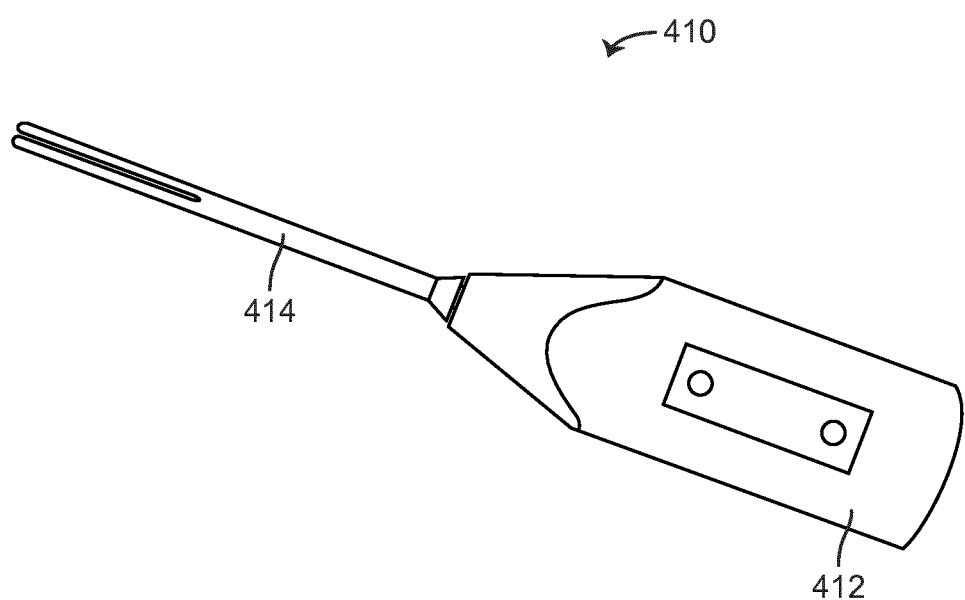
FIG. 5 illustrates a mixing apparatus according to an exemplary embodiment.

Referring to FIG. 5, in an exemplary embodiment, mixing and delivery system 400 also includes a mixing apparatus 410. The mixing apparatus 410 may be a blender or other device suitable for mixing the particulate solid with the mixing liquid. The mixing apparatus 410 may be any blender, agitator, or mixer suitable for mixing medical substances. As shown in the embodiment of FIG. 5, the mixing apparatus 410 includes a handle/housing portion 412 for managing and manipulating the mixing apparatus 410 and a mixing portion 414. The mixing portion 414, as shown, is an elongated portion that is configured to be received through the inlet portion of the compressible tube 401, such that the mixing and forming of the surgical substance can take place within the reservoir 402.

Figure 6:
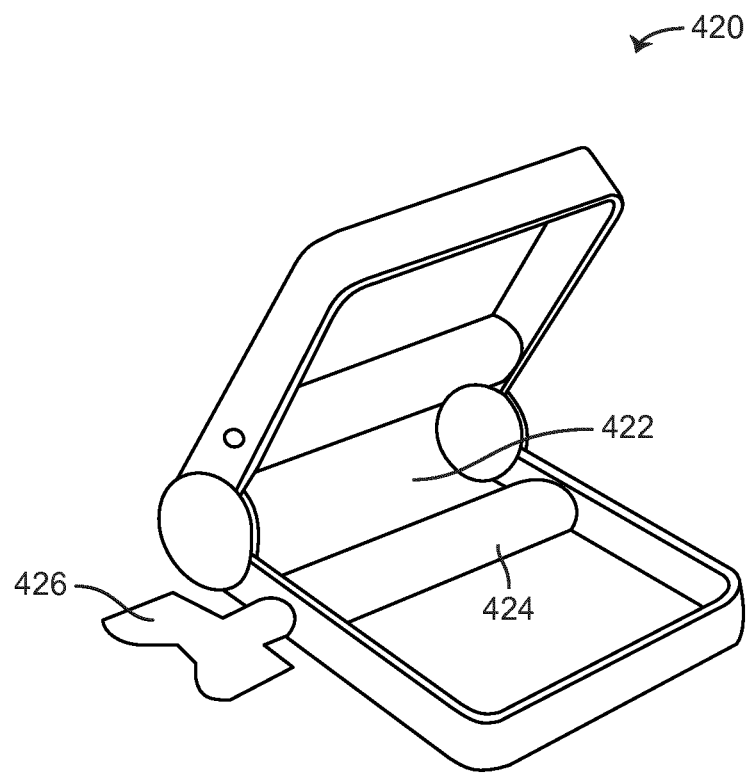
FIG. 6 illustrates a pinching apparatus to be used with the delivery system according to an exemplary embodiment.
Figure 7:
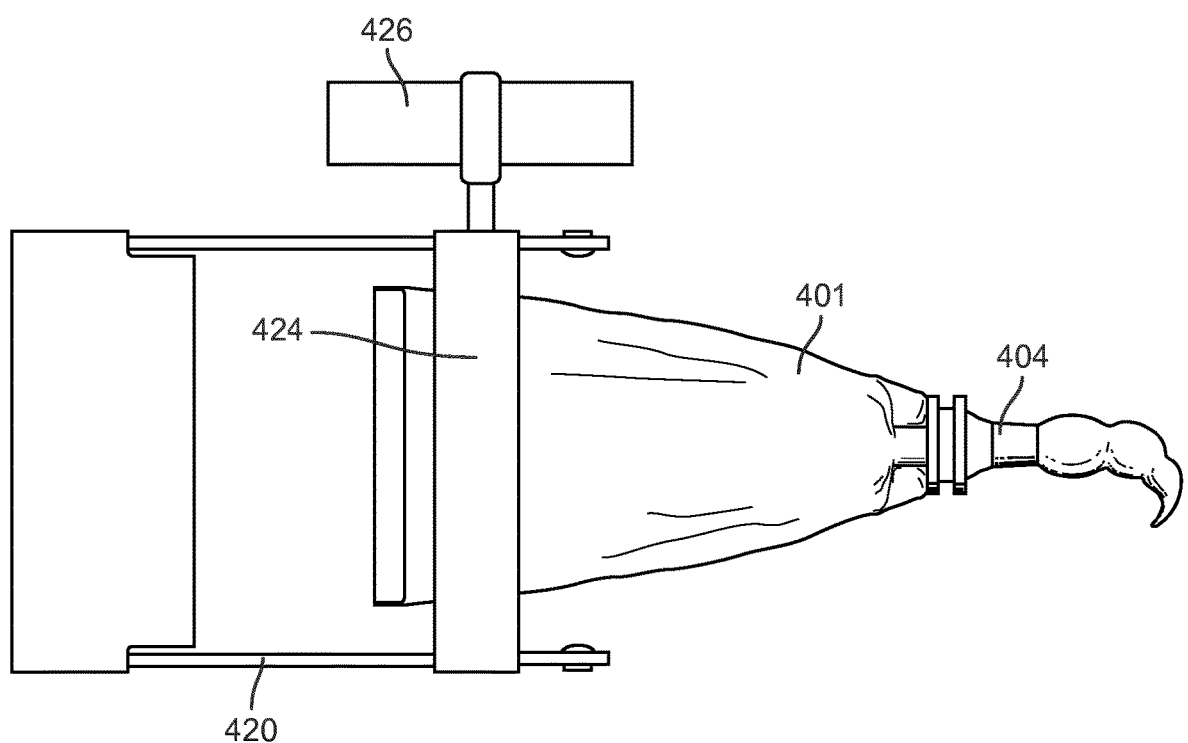
FIG. 7 illustrates a pinching apparatus used on the compressible tube in accordance with an exemplary embodiment of the delivery system.

Mixing and delivery system 400 may also include a compressing device, such as the compressing device 420 shown in FIG. 6. The compressing device 420 may have a slotted portion 422 configured to receive a portion of the compressible tube 401 therethrough. The compressing device 420 may be separate from the compressible tube 401, or may be integrated into the compressible tube 401. The compressing device 420 is configured to move along the length of the compressible tube 401, compressing the compressible tube 401 so as to force the surgical substance through the exit portal of the compressible tube 401, as shown in FIG. 7, and to the cannula, catheter, needle, or other chosen delivery apparatus. In particular, the compressing device 420 may have a rolling key 424 that moves along or rolls the compressible tube 401 by way of manual manipulation of a key flange 426, and that causes the compression of the compressible tube 401 and forces the surgical substance from the reservoir 402.

One method of mixing and delivering a surgical substance to bone, such as a bone void filler, according to an exemplary embodiment includes providing a compressible delivery tube, such as compressible tube 401, wherein the compressible tube 401 has a reservoir 402. The compressible tube 401 may be provided with a first element therein, such as particulate solid or a prepared paste or fluid, or the first element may be introduced into the reservoir 402 through the portal 404. A mixing apparatus 410, such as a blender, mixing, or agitator, is introduced to the reservoir 402 of the compressible tube 401 after or during introduction of a second element, such as the mixing liquid to the reservoir 402. As described above, the second element, such as the mixing liquid, may be introduced through the portal 404 or through an alternative inlet portion of the compressible tube 401. The mixing apparatus 410, likewise, may be introduced through the portal 404 or through an alternative inlet portion of the compressible tube 401. The method further includes moving the surgical substance through the exit port of the compressible tube 401 for delivery to the body. Delivery to the body may take place through a cannula as described above, or may alternatively take place through a catheter, delivery needle, or other delivery apparatus. Moving the surgical substance through the exit port of the compressible tube 401 may use a compressing device 420 which moves along the length of the compressible tube 401 to force the surgical substance through the portal 404 of the compressible tube 401.

The construction and arrangement of the devices and methods as shown in the various exemplary embodiments are illustrative only. Although only a few embodiments have been described in detail in this disclosure, many modifications are possible (e.g., variations in sizes, dimensions, structures, shapes and proportions of the various elements, use of materials, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A method of mixing and delivering a substance to a bone, comprising:
   providing a compressible tube having a reservoir and an exit portal, the compressible tube containing at least a first substance element therein;
   introducing a second substance element to the first substance element;
   introducing a mixing apparatus into the reservoir through the exit portal;
   mixing the first substance element and the second substance element using the mixing apparatus to form the substance within the reservoir of the compressible tube;
   removing the entirety of the mixing apparatus from the reservoir; and
   delivering the substance through the exit portal in the compressible tube for delivery to the bone using a compressing device.

2. The method of claim 1, wherein the first substance element is a particulate solid and the second substance element is a mixing liquid.

3. The method of claim 1, further comprising introducing the second element into the reservoir of the compressible tube.

4. The method of claim 1, further comprising moving the substance through the exit portal and into a delivery apparatus for delivery directly to the bone.

5. The method of claim 4, wherein the delivery apparatus is a cannula positioned within the body and having a distal portion position near a target portion of the bone.

6. The method of claim 1, wherein the substance is a bone void filler.

7. The method of claim 1, wherein the compressing device is positioned on the compressible tube and wherein the method further comprises moving the compressing device along the compressible tube to empty the substance from the compressible tube.

8. The method of claim 7, wherein the compressing device comprises a rolling key to roll the compressible tube to empty the substance from the compressible tube.

9. The method of claim 1, wherein the second element is introduced to the reservoir through a sealable inlet portion.

10. The method of claim 9, wherein the compressible tube further comprises a portal comprising the sealable inlet portion and the exit portal.

11. The method of claim 1, wherein the first element is selected from the group consisting of stem cells and a bone marrow aspirate.

12. The method of claim 1, wherein the first element is a paste material and the second material is a mixing liquid.

* * * * *